(12) United States Patent
Gitis et al.

(10) Patent No.: US 7,118,577 B2
(45) Date of Patent: Oct. 10, 2006

(54) MULTIPORTAL DEVICE WITH LINKED SEGMENTED CANNULAE AND METHOD FOR PERCUTANEOUS SURGERY

(75) Inventors: Norm Gitis, Cupertino, CA (US); Todd F. Alamin, San Mateo, CA (US); Aleksandr Meyman, Belmont, CA (US); Oleg Shulepov, Santa Clara, CA (US); Mikhail Faynberg, San Jose, CA (US)

(73) Assignee: Nevmet Corporation

( * ) Notice: Subject to any disclaimer, the term of this patent is extended or adjusted under 35 U.S.C. 154(b) by 633 days.

(21) Appl. No.: 10/146,304

(22) Filed: May 16, 2002

(65) Prior Publication Data

US 2003/0216768 A1  Nov. 20, 2003

(51) Int. Cl.
*A61B 17/56* (2006.01)
*A61M 39/10* (2006.01)
(52) U.S. Cl. .................. 606/87; 606/86; 604/264
(58) Field of Classification Search .......... 604/533, 604/538, 240–242, 510, 264; 606/87, 108; 600/114
See application file for complete search history.

(56) References Cited

U.S. PATENT DOCUMENTS

| | | | |
|---|---|---|---|
| 4,545,374 A | | 10/1985 | Jacobson |
| 5,084,043 A | | 1/1992 | Hertzmann et al. |
| 5,301,658 A | * | 4/1994 | Zhu et al. ............... 606/191 |
| 5,437,661 A | | 8/1995 | Rieser |
| 5,730,754 A | | 3/1998 | Obenchain |
| 5,762,629 A | | 6/1998 | Kambin |
| 5,882,344 A | * | 3/1999 | Stouder, Jr. ............... 604/264 |
| 6,070,589 A | * | 6/2000 | Keith et al. ............... 606/198 |
| 6,228,022 B1 | | 5/2001 | Friesem et al. |
| 6,254,553 B1 | | 7/2001 | Lidgren et al. |
| 6,264,650 B1 | | 7/2001 | Hovda et al. |

OTHER PUBLICATIONS

U.S. Patent Application mailed to USPTO on Apr. 30, 2002, N. Gitis et al., not yet registered.
U.S. Patent Application mailed to USPTO N. Gitis et al, not yet registered.
Clinical Anthopaedics and Related Research, No. 238, 1989 (By A. Shreiber et al).

* cited by examiner

*Primary Examiner*—Julian W. Woo
*Assistant Examiner*—Sarah Webb

(57) ABSTRACT

The device of the invention consists of a plurality of tubular cannulae, consisting of stackable segments, which prior to the surgery, are linked together at their distal ends by flexible elements, such as wires or threads. All the threads, the number of which is one less than the number of the used cannulae, are passed through one of the cannulae and the distal ends of the threads are either attached to the walls of other cannulae, at their distal ends, or pulled back through one of the cannula forming the loop at the distal end and fixed at the proximal end of the cannula. During surgery, the cannulae with their distal ends being linked are inserted into the patient's body through an incision, then the surgeon makes additional incisions, disconnects some segments from selected cannulae, subcutaneously pulls them to the additional incisions, and reconnects previously disconnected segments. The surgery is then performed using the cannulae for guiding various surgical tools. Due to flexible linking of the cannulae at their distal ends, the cannulae can be easily manipulated without disconnection and without a need for use of extraneous X-raying for reorientation of the cannulae.

42 Claims, 14 Drawing Sheets

MULTIPORTAL DEVICE WITH LINKED SEGMENTED CANNULAE AND METHOD FOR PERCUTANEOUS SURGERY

FIELD OF THE INVENTION

This invention relates to the field of medicine, in particular to surgery, and specifically to a method and a device for access and removal of prolapsed nucleus pulposus material of a herniated intervertebral disc through the spinal foramen.

BACKGROUND OF THE INVENTION

Low back pain and radiculopathy as a result of herniated intervertebral disc represents a major health problem in the United States and all over the world. About 300,000 Americans and about the same number of people throughout the world outside the USA are operated upon each year due to this problem. Even many more people might benefit from surgical help, as those that undergo such surgery represent only about 20% of those with pathology referable to the intervertebral disc.

An intervertebral disc is a structure that occupies the space between the vertebrae. It serves, in particular, as a load-absorbing cushion.

FIG. 1 is a cross-sectional view of a vertebral column through a healthy intervertebral disc 20, and FIG. 2 is a side view on a part of the vertebral column illustrating the position of the disc 20. As can be seen from FIGS. 1 and 2, the disc 20 consists of two parts: a ring-like external part 22, known as "annulus" (or "annulus fibrosis"), and an internal, central part 24, known as "nucleus" (or "nucleus pulposus"). The tissue of the annulus 22 degenerates with age or as a result of some injuries or illnesses. When annulus 22 degenerates, its fibers weaken, and external forces, applied to the adjacent vertebrae, can cause the rupture of the annulus fibers, and nucleus tissue protrusion, shown in FIGS. 3 and 4 that correspond respectively to FIGS. 1 and 2. This creates a disc herniation 26 (FIG. 3), which, in turn, may cause a pressure on the adjacent nerve root 28 (FIGS. 1 and 3), resulting in pain.

It is understood that herniation may occur in any other part of the disc and cause different symptoms and that the herniation position shown in FIGS. 3 and 4 is given just as an example.

At the present time, several approaches exist for treatment of the problem described above. The first method is called "laminectomy". This is a surgical procedure, which involves accessing a symptomatic disc by excising a significant amount of the vertebral lamina, followed by removal of the herniated disc material. A laminectomy is a somewhat destructive procedure, which might cause extensive scarring and long (up to 9 days) hospitalization, with an up to 3-month postoperative recovery period.

Another approach is called "microlumbar surgery" ("microsurgical discectomy", or "microdiscectomy"). It is similar to laminectomy in that the disc is accessed through an incision made on the patient's back and developed into a channel to the symptomatic disc. Unlike laminectomy, the microdiscectomy employs a microscope, allowing a smaller incision (about 2 times less than during the laminectomy). This method permits a surgeon to use microsurgical tools, and avoid much of the bone dissection. This is less invasive compared to the laminectomy, though the existing microdiscectomy may still cause some complications similar to those associated with laminectomy, for example, possible injury to the nerve root and dural sac, postoperative scarring and a relatively long recovery time. Furthermore, the paraspinal musculature must still be retracted out to the level of the facet for the duration of the procedure.

Other methods of treatment consist of a removal of the disc nucleus tissue either by suction or by dissolving it. The former approach (suction) is known as a percutaneous discectomy and is carried out by utilizing hollow needles of special design, which are placed through the back muscles into the center of the disc (into the nucleus area) and then allow suction of the tissue. The latter approach (dissolving) is known as chemonucleolysis, which is carried out by injecting a special enzyme (chymopapain) into the center of the disc. The chemonucleolysis may cause severe pain, spasms, and anaphylactic shock (the mortality rate associated with chemonucleolysis has been estimated at about 0.5%). Both approaches belong to so-called Minimally Invasive Spinal Surgery (hereinafter referred to as MISS) methods. As a result of removal of the disc nucleus tissue, the protruded disc material can then collapse back inside, toward the center of the disc, which can in turn, reduce the pressure on the spinal nerve roots.

Many attempts have been made heretofore to improve methods and surgical instruments employed in the percutaneous discectomy procedures.

For example, U.S. Pat. No. 4,545,374 issued in 1985 to R. Jacobson discloses a method and instruments for performing a percutaneous lumbar discectomy. The method consists in accessing the lumbar region of the spinal column by laterally inserting a cannula through the patient's side above the iliac crest to contact a predetermined position in the lumbar region and passing instruments through the cannula. This method is useful for performing percutaneous lumbar discectomy by cutting a portion of the patient's disc annulus and nucleus through the cannula and removing a desired amount of nucleus material. The cannula has a tubular member and anchor means attached to one end of the member for anchoring the cannula in the body tissue to prevent shearing movement between it and the tissue. Other instruments for performing a percutaneous lumbar discectomy are disclosed, including a speculum and trocar for percutaneously inserting the cannula into the patient, a discectomy knife for cutting disc nucleus material and rongeur forceps for removing the disc material. The above instruments may be combined in a surgical apparatus.

The method of U.S. Pat. No. 4,545,374 has the following drawbacks: 1) the material is removed from the center of the disc only, thus preventing a surgeon from excising the fragments from the actual herniation site, which may or may not cause recurrent symptoms; 2) this technique is unsuitable for noncontained (or sequestered) herniations, since it does not give a surgeon access to the epidural space.

U.S Pat. No. 5,084,043 issued in 1992 to P. Hertzmann et al. describes laser-assisted disc decompression (LDD). It utilizes a high-energy laser beam to vaporize the affected tissue instead of removing it mechanically. Like in the percutaneous approach described above, one of the disadvantages inherent in this procedure is that it deals with the disc nucleus, rather than with the herniation itself.

Several MISS methods, based upon contemporary technology achievements, were introduced during last 10–15 years. For instance, U.S. Pat. No. 5,437,661 issued in 1995 to B. Rieser discloses a method for removal of prolapsed nucleus pulposus material on an intervertebral disc by using a laser. A cannula is inserted into the spinal foramen. Once the cannula has passed the ligamentum flavum, a laser fiber is inserted into it. The laser fiber contacts the prolapsed material and a laser beam substantially eliminates the prolapsed material within the spinal foramen.

Lasers are both expensive and somewhat tedious to use in these procedures. Another disadvantage with lasers is the difficulty in judging the depth of tissue ablation. Since the surgeon generally points and shoots the laser without contacting the tissue, he or she does not receive any tactile feedback to know how deeply the laser is cutting. Because healthy tissue, bones, ligaments, and spinal nerves often lie in the close proximity to the spinal disc, it is essential to maintain a minimal depth of tissue damage, which cannot always be ensured with a laser.

U.S. Pat. No. 6,264,650 issued in 2001 to D. Hovda et al. describes systems, apparatus, and methods for ablation, resection, aspiration, collagen shrinkage, and/or hemostasis of tissue and other body structures in open and endoscopic spine surgery. In particular, the invention includes a channeling technique, in which small holes or channels are formed within spinal discs, and thermal energy is applied to the tissue surface immediately surrounding these holes or channels to cause thermal damage to the tissue surface, thereby stiffening the surrounding tissue structure and reducing the volume of the disc to relieve pressure on the surrounding nerves, and thereby relieving neck or back pain.

U.S. Pat. No. 6,254,553 issued in 2001 to L. Lindgren et al. offers a method and a device for non-invasive treatment of biological tissue by changing or degenerating the tissue. This device has a treatment transducer for treating intervertebral discs, preferably nucleus pulposus, by ultrasound. The ultrasonic field of the ultrasonic transducer is focused in the symptomatic intervertebral disc, preferably in nucleus pulposus of this disc, for heating the tissue to such a temperature that the tissue in the focal area degenerates, whereby the pressure in the intervertebral disc, and thus the pressure against the spinal nerve roots, is reduced.

Both methods described in U.S. Pat. No. 6,264,650 and in U.S. Pat. No. 6,254,553 make it complicated for a surgeon to focus treatment on the symptomatic site, without affecting the surrounding tissues.

Single-portal MISS methods are limited to the use of one channel at a time. It was suggested to introduce a second portal to the annulus as described by Shreiber et al. in Clinical Orthopaedics and Related Research No. 238. However, this biportal procedure assumes the second portal to be created from the opposite side to the first portal (bilateral), hence increasing the operating time, post-operative morbidity, and surgeon exposure to radiation. It may also cause excessive removal of disc nuclear tissue, therefore increasing the possibility of post-operative stenosis (narrowing) of the foramen.

Therefore, there is a need for a unilateral multiportal approach for the percutaneous disc procedures. Such attempts were made by either using an oval cannula, which allows using several tools at a time (see U.S. Pat. No. 6,228,022 issued on May 8, 2001 to T. Friesem et al, and U.S. Pat. No. 5,762,629 issued on Jun. 9, 1998 to P. Kambin), or introducing a second cannula for a biportal unilateral approach (the U.S. Pat. Nos. 5,762,629 and 5,730,754 issued on Mar. 24, 1998 to T. Obenchain). These approaches do not provide a comprehensive solution for percutaneous disc surgery. The method described in U.S. Pat. No. 5,730,754 still needs accurate targeting and it not sufficiently universal. U.S. Pat. No. 5,762,629 allows inserting a second cannula using a special targeting device, but has the following disadvantages: 1) the targeting device is rigid and does not allow the flexibility required by a surgeon for the formation of an angle between inserted cannulae; 2) after cannulae are inserted, the targeting device is removed, leaving the cannulae completely unlinked, so that a surgeon cannot keep them interrelated. In case the position of one of the inserted cannulae should be temporarily changed, it becomes a problem to reorient them, especially when more than two cannulae are used for the surgery.

Another common disadvantage of the existing devices for the percutaneous surgery is that they require the operation to be carried out under X-ray monitoring at all steps of the surgery, i.e., during insertion of each additional cannula and occasionally during the procedure itself. Simultaneously used cannulae are not interrelated with regard to their relative movements, once a cannula is shifted from its original position aligned under X-ray or by means of a special guiding device, it cannot be returned back to the original position, unless X-ray is used again. Such multiple X-ray monitoring exposes both the surgeon and the patient to an increased doze of radiation.

The problems associated with known percutaneous surgery devices were solved with the use of a multiportal device for percutaneous surgery developed by the applicants and described in our pending U.S. patent application Ser. No. 10/136,548 filed on May 1, 2002. The device disclosed in the aforementioned patent application consists of a guiding mechanism with a radial arm that supports an auxiliary guiding device, which can slide along the arm and can be fixed in a require angular position on the arm. The device also includes a first cannula, which can be inserted into the patient's body through the guiding device and can be fixed in a required axial position, and a second cannula, which can be inserted into the auxiliary guiding device and fixed therein. The arch-shaped form of the arm ensures intersection of distal ends of both cannulae in one point aimed at the symptomatic site where surgery has to be done. The device is provided with a linking mechanism that links the distal ends of both cannulae in their position inside the body of a patient. When the linking device is in the engaged state, the cannulae still have some freedom of relative movements that may be required for manipulation with cannulae during the surgery. The invention also relates to a method of using the multiportal device for percutaneous surgery. The device allows insertion of a plurality of cannulae and permanently maintaining them in controlled positions without resorting to additional X-ray. The internal linking mechanism of the above device consists of moveable parts, which have to be engaged inside the patient's body close to the sensitive areas. In particular, in the embodiments described, the internal linking mechanism consists of a rod located inside one of the cannulae and a hook-like loop located in a neighboring cannula.

Although the device described above is efficient in eliminating extraneous X-raying and in facilitating guiding and manipulation of the cannulae during multiportal approach to the symptomatic site, nevertheless this device has many parts and is expensive to manufacture. Such a device is normally made of metal in view of provision of springs, loop-like hook, windows on the distal ends of the cannulae, etc. Therefore it cannot be made entirely of plastics and cannot be made disposable.

The solution of last-mentioned problems was presented in another pending U.S. patent application Ser. No. 10/145,488 filed on May 15, 2002 by the same applicants. The device disclosed in this patent application consists of a plurality of tubular cannulae, which prior to the surgery, are linked together at their distal ends by flexible elements, such as wires or threads. All the threads, the number of which is one less than the number of the used cannulae, are passed through one of the cannulae, and the distal ends of the threads are attached to the walls of other cannulae, at their distal ends. During surgery, the cannulae with their distal ends being linked are inserted into the patient's body through an incision and then the cannulae are used for guiding various surgical tools. Due to flexible linking of the cannulae at their distal ends, the cannulae can be easily manipulated without disconnection and without a need in extraneous X-raying for reorientation of the cannulae. The aforementioned patent application also relates to a method of using the multiportal device for percutaneous surgery.

The construction of the device disclosed in the above application envisages an angular arrangement of the cannulae inserted into the patient's body. This is because the surgeon needs a freedom of manipulation with the cannulae during the surgery. However, when the surgery is performed on relatively flat portions of the patient's body, e.g., on overweight patients with posterolateral access to the symptomatic site, in order to provide the aforementioned freedom for cannula manipulation, the surgeon will have to make a large incision. This may cause more extensive scarring and longer healing.

OBJECTS AND SUMMARY OF THE INVENTION

It is an object of the present invention to provide a multiportal device with linked segmented cannulae for percutaneous surgery, which is very simple in construction, reliable and simple in use, allows insertion of cannulae and permanently maintaining them in controlled positions without resorting to additional X-ray for the duration of the procedure. It is another object to provide a device and method that allow performing a surgery with short incisions. It is a further object of the invention to provide a device and method, which ensure angular arrangement of cannulae inserted into the patient's body even on relatively flat portions of the body.

The device of the invention consists of a plurality of tubular cannulae, which prior to the surgery are linked together with flexible elements, such as wires or threads. Some of the cannulae consist of several stackable segments, so that the length of these cannulae can be reduced or increased by connecting or disconnecting the segments. All the threads are passed through one of the cannulae and the distal ends of the threads are attached to the walls of other cannulae, at their distal ends. During surgery, the cannulae with their distal ends being linked are inserted into the patient's body through an incision and then the cannulae are used for guiding various surgical tools. Due to the flexible linking of the cannulae, they can be easily manipulated without disconnection and without a need for extraneous X-raying for their reorientation. When it is necessary to avoid making a wide incision, the surgeon first makes a short incision sufficient just to fit the front ends of all pre-linked and pre-packed cannulae into this short incision, and then shortens the length of specific cannulae to the extent that would allow their subcutaneous manipulation. The surgeon makes additional short incisions, pulls the shortened cannulae subcutaneously to their respective additional incisions by means of a special pulling tool, and exposes the cannulae into their respective additional incisions. Following this, the cannulae protruded through the additional incisions are extended to a required length by connecting the segments. Thus, the device is ready for performing the surgery with freedom of cannula manipulation without additional X-raying and without making large incisions.

DETAILED DESCRIPTION OF THE INVENTION

Figure 5:
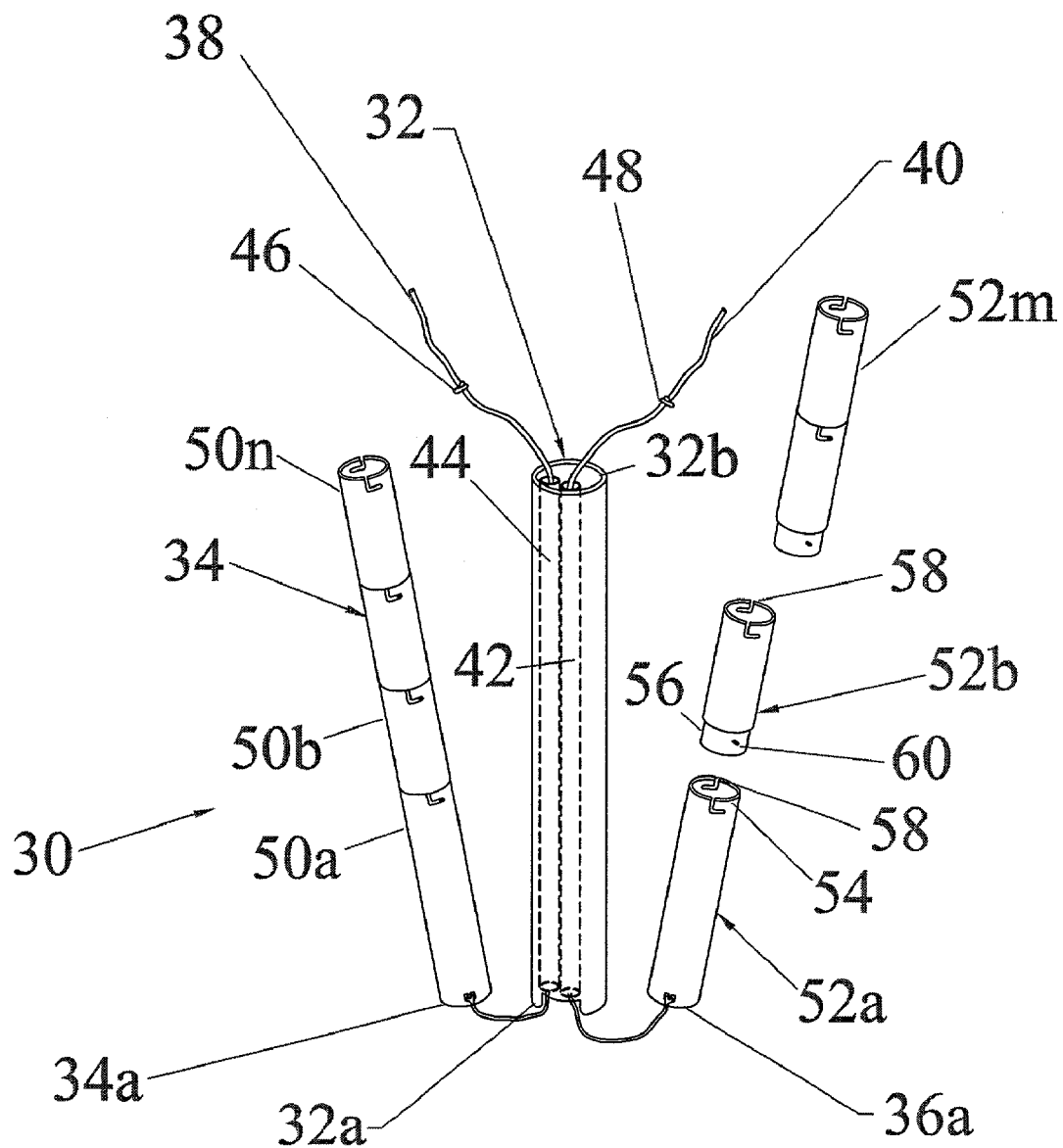
FIG. 5 is a schematic three-dimensional view of a device of the invention consisting of three working cannulae, two of which comprising stackable segments.

A general three-dimensional view of the multiportal device with linked segmented cannulae of the invention for percutaneous surgery (hereinafter referred to as "multiportal device") is shown in FIG. 5. In the embodiment shown in this drawing, the multiportal device, designated in general by reference numeral 30, consists of three linked cannulae 32, 34, and 36. It is understood that these three cannulae are shown only as an example and that the principle of the invention is equally applicable to the embodiments with two or more than three cannulae. The device per se is very simple and consists of a required number of cannulae 32, 34, and 36, in the illustrated case, pre-linked at their distal ends 32a, 34a, and 36a, respectively, with flexible elements such as wires or threads 38 and 40. More specifically, both threads 38 and 40 are passed through the central cannula 32 and their ends that project through the distal end 32a, are secured to the walls of the neighboring cannulae 34 and 36 respectively. As shown in FIG. 5, in order to prevent interference of the threads inside the cannula 32 with the surgical instruments guided through the cannula 32 and protect the threads from entanglement or the like, both threads 38 and 40 are additionally guided through individual small-diameter tubes 42 and 44, respectively, which have diameters significantly smaller than the inner diameter of the cannula 32 and which are attached to the inner wall of the cannula 32. In order to prevent full penetration of the threads 38 and 40 below the proximal end 32b of the cannula 32, each thread has a stopper 46 and 48, respectively, e.g., in the form of a large knot. In the embodiment of FIG. 5, the lower ends of the threads 38 and 40 are secured to the walls of the respective cannulae 34 and 36, preferably close to their distal ends 34a and 36a. Connection can be made by fusion, welding, riveting, etc. The connection should not interfere with the insertion of surgical tools through the respective cannula. Cannulae 34 and 36, in turn, consist of several stackable segments. More specifically, the cannula 34 consists of segments 50a, 50b, . . . 50n, while the cannula 36 consists of segments 52a, 52b . . . 52m. Among these segments, the lowermost segments, i.e., 50a and 52a are different in design from the rest of the segments 50b . . . 50n and 52b . . . 52m, which are used for adjusting the total length of the respective cannulae by being connected to the lowermost segments 50a and 52a and then to each other in series in the axial direction of the cannula (FIG. 5) until a required length is achieved. The segments may be connected, e.g., by telescopically inserting the lower end 56 of one segment with tight fit into the upper end 54 of the preceding segment, as shown in FIG. 5, or may be connected and locked, e.g., by using a bayonet-type connection formed by grooves 58 on the upper ends 54 and pins 60 on the lower ends 56 of the connectable segments.

A percutaneous surgical procedure with the use of the device 30 of the invention will now be described with reference to FIGS. 6 through 17, which illustrate sequential steps of the surgery, e.g., intervertebral disc discectomy.

Figure 1:
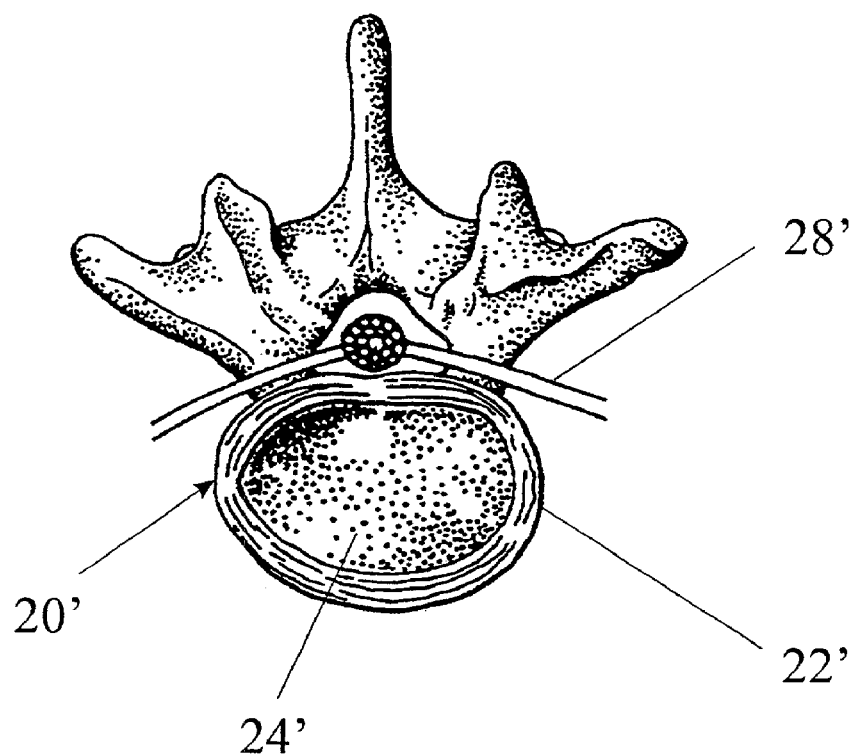
FIG. 1 is a cross-sectional view of a vertebral column through a healthy intervertebral disc.
Figure 2:
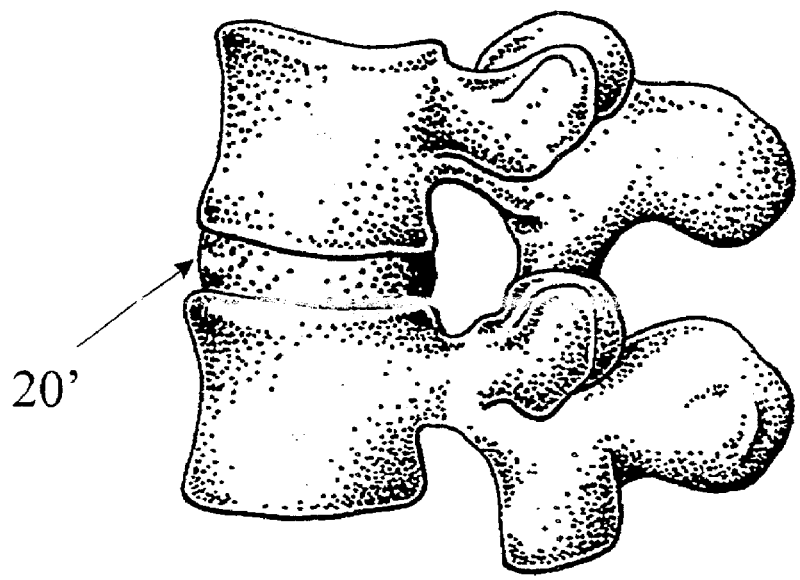
FIG. 2 is a side view on a part of the vertebral column illustrating the position of the disc of FIG. 1.
Figure 3:
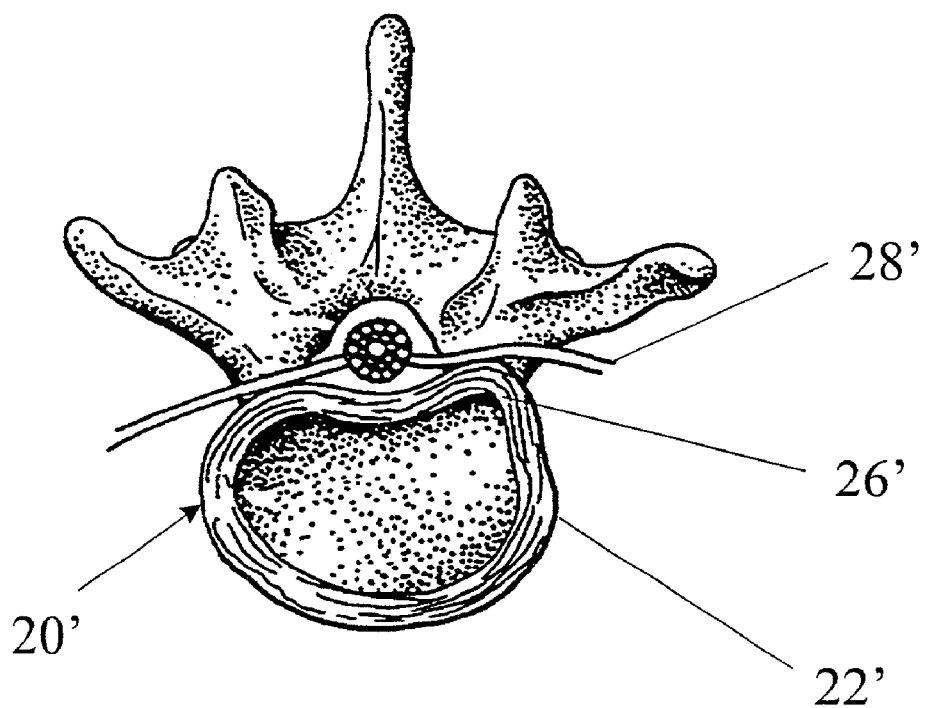
FIG. 3 is a view similar to FIG. 1 illustrating a herniated disc that may require an operation.
Figure 4:
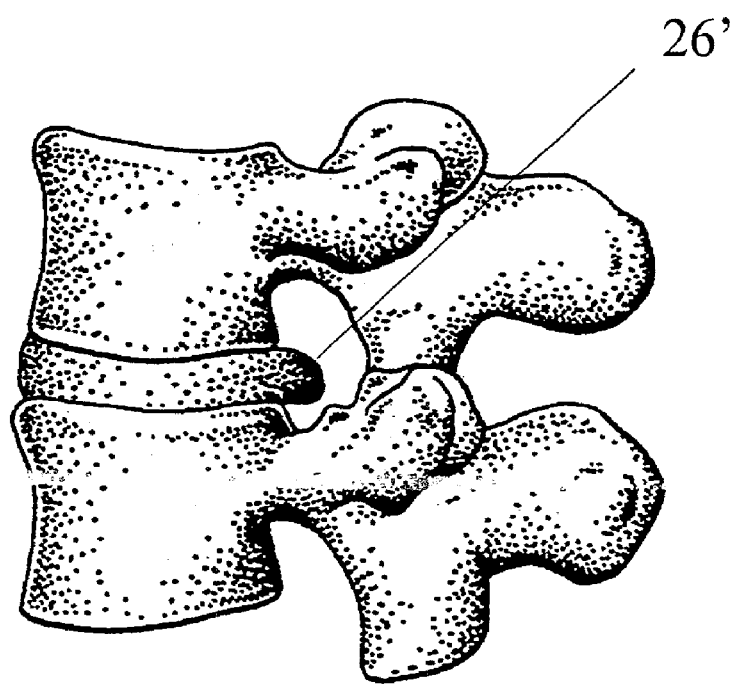
FIG. 4 is a side view similar to FIG. 2 illustrating a herniated disc protruded into the foramen.
Figure 6:
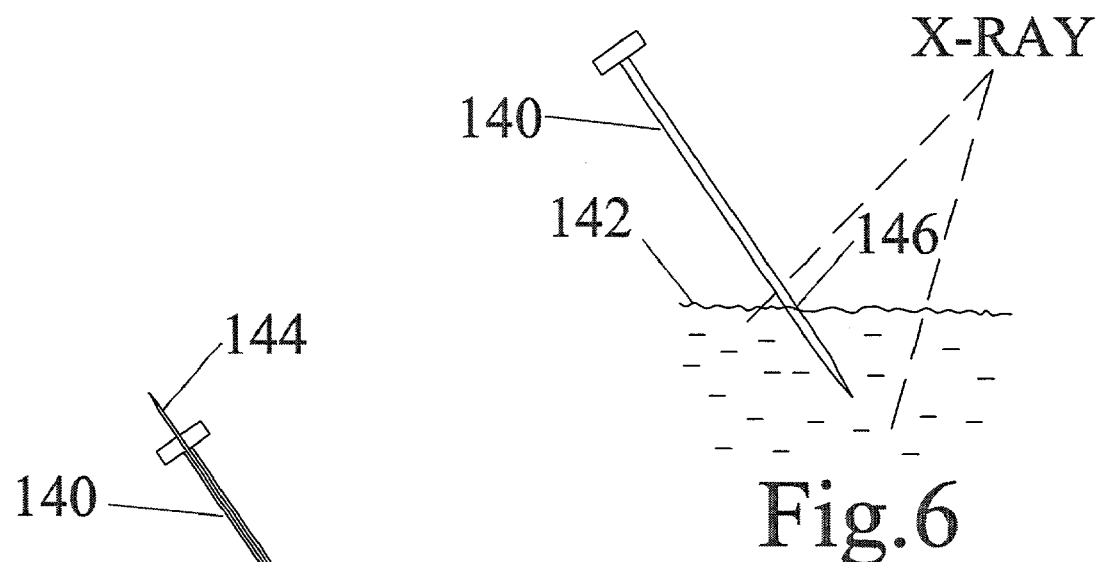
FIG. 6 shows a special needle with a bore inserted into the patient's body.
Figure 7:
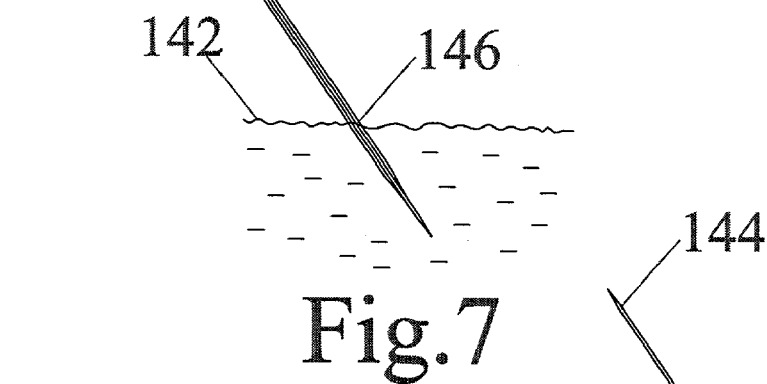
FIG. 7 is a view similar to FIG. 6 illustrating a guidewire inserted into the central bore of the needle shown in FIG. 6.
Figure 8:
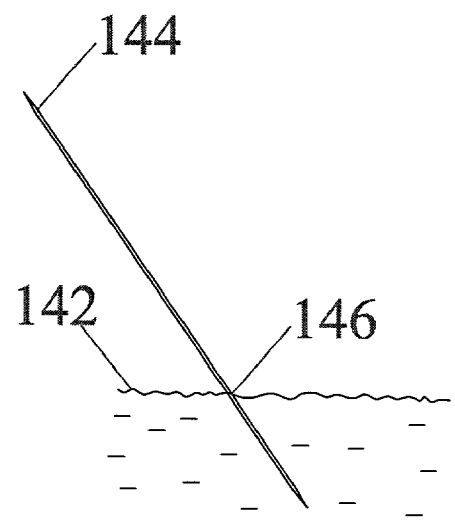
FIG. 8 is a view similar to FIG. 7 with the special needle removed and the guidewire left in the patient's body.

After being diagnosed as having a prolapsed disc causing a nerve root impingement of the type shown in FIGS. 3 and 4, the patient is positioned on a radiolucent table (not shown) in a prone position. First, a surgeon inserts a special needle 140 with a bore (not shown) into the patient's body over the symptomatic site, as shown in FIG. 6. The needle 140 is rigid enough to stay straight and helps the surgeon to get to a desired position inside the patient's body 142 under the fluoroscopic guidance. Under the fluoroscopic observation, a guidewire 144 made of suitable stainless steel of about 1.0 to 1.25 mm in diameter is inserted through the bore of the needle 140 into the patient's body 142 through a predefined entry point 146. This is shown in FIG. 7, which illustrates a guidewire inserted into the central bore of the needle shown in FIG. 6. The guidewire 144 is advanced until it reaches the target position specified by the surgeon. After the guidewire 144 is in the right position, the needle 140 is removed from the patient's body, and a surgeon does an incision around the entry point 146 in order to be able to insert other tools. FIG. 8 is a view similar to FIG. 7 with the special needle removed and the guidewire left in the patient's body.

Figure 9:
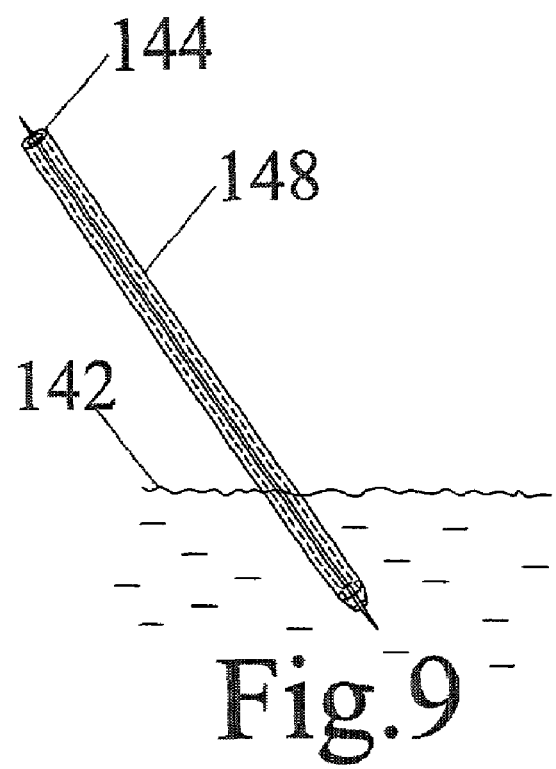
FIG. 9 is a view similar to FIG. 8 illustrating an obturator fitted over the guidewire.

The next step is shown in FIG. 9, which is similar to FIG. 8 and illustrates an obturator fitted over the guidewire. At this time, a cannulated obturator 148 with a lumen, diameter of which is slightly larger than the diameter of the guidewire 144, is passed over the guidewire 144 through the patient's skin until a distal end of the obturator 148 reaches the same position as the guidewire 144. At this step, the guidewire 144 may or may not be removed.

Figure 10:
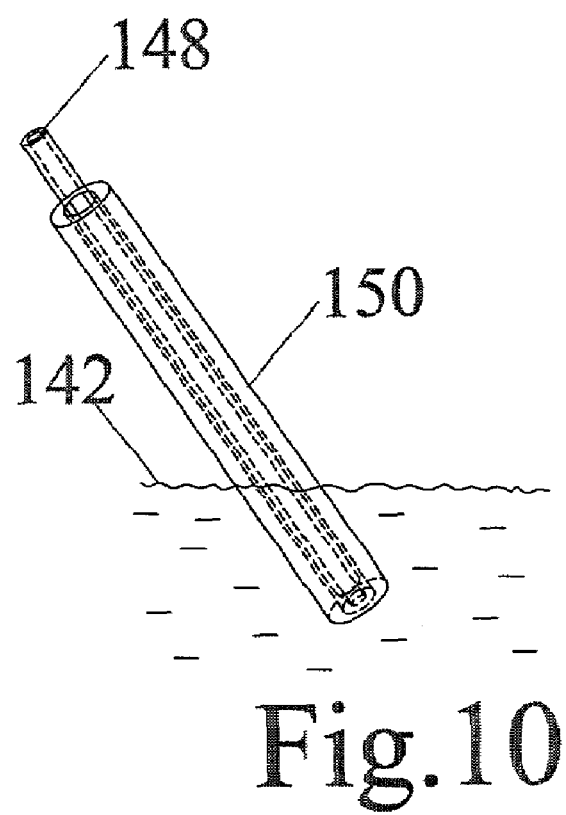
FIG. 10 is a view similar to FIG. 9 with a large-diameter cannula fitted onto the obturator, the guidewire being removed.
Figure 11:
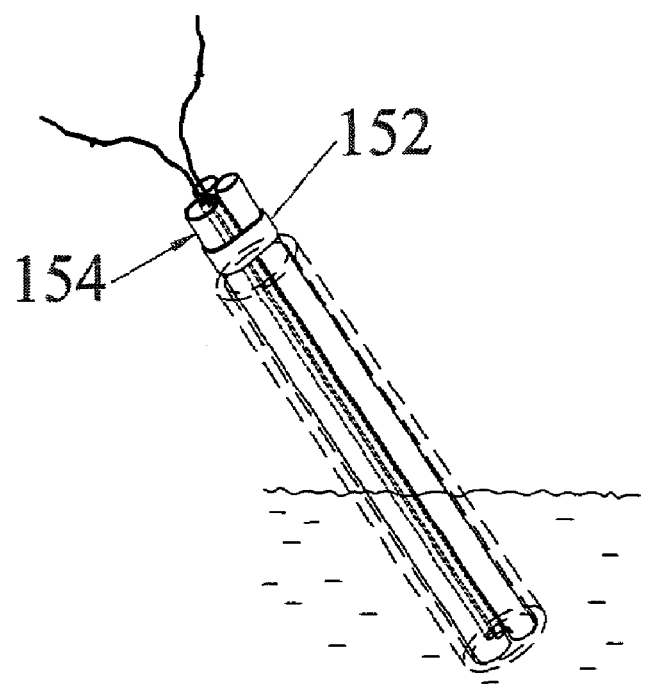
FIG. 11 is a three-dimensional view of a cannula pack inserted into the large-diameter cannula.

FIG. 10 is a view similar to FIG. 9 with a large-diameter cannula fitted onto the obturator, the guidewire being removed. FIG. 11 is a three-dimensional view of a cannula pack inserted into the large-diameter cannula.

Figure 12:
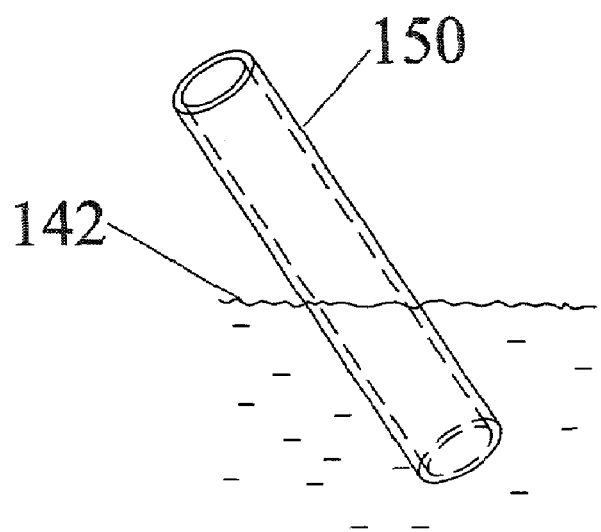
FIG. 12 is a view similar to FIG. 10 with the obturator removed from the patient's body.

A large-diameter cannula 150, which is shown in FIG. 10, may accommodate all working cannulae (which in the illustrated embodiment are cannulae 32, 34, and 36 bound into a single pack shown in FIG. 11). The cannula 150 is fitted onto the obturator 148, and then advanced over the obturator 148 until the distal end of the cannula 150 reaches the position of the distal end of the obturator 148. At this time, both the obturator 148 and the guidewire 144 (if it has still not been removed) are removed. The position of the cannula 150 inserted into the patient's body 142 with the obturator 148 and the guidewire 144 removed is shown in FIG. 12.

Figure 13:
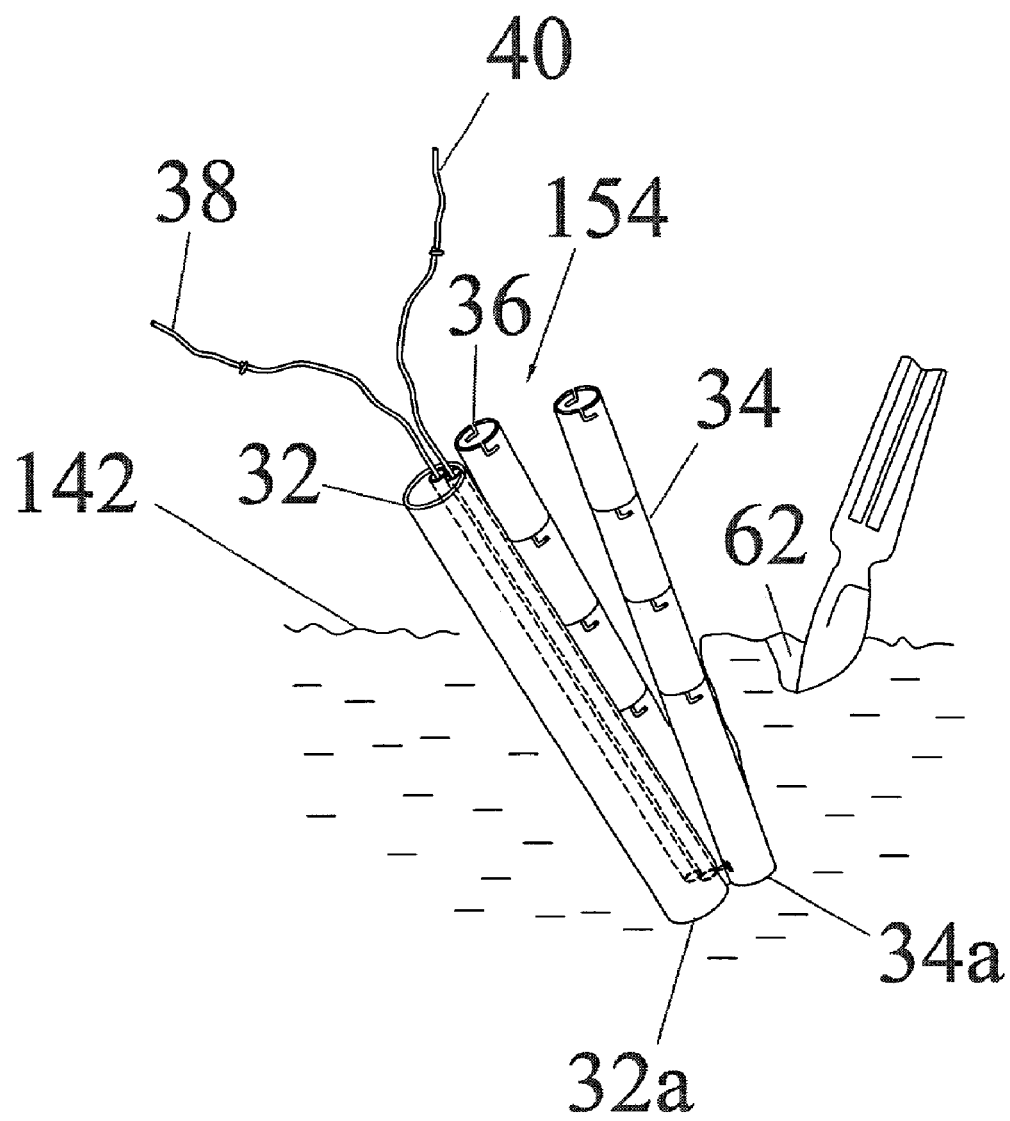
FIG. 13 is a three-dimensional view of the working cannulae after insertion into the body of a patient and the second incision being made.

As mentioned above, the working cannulae 32, 34, 36 are packed into a single unit, e.g., by fixing them together with a binding element such as a rubber band 152 shown in FIG. 11. In this drawing, the entire pack is designated by reference numeral 154. The cannula pack 154 is inserted into the large-diameter cannula 150 till the distal ends of the working cannulae 32, 34, 36 reach the distal end of the large-diameter cannula 150. The large-diameter cannula 150 is then removed from the patient's body 142 and, hence, from the cannula pack 154 (this step is not shown). The cannulae 32, 34, 36 are released from the binding element 152. However, as shown in FIG. 13, which is a three-dimensional view of the working cannulae after insertion into the body of a patient, the distal ends 32a, 34a of the respective working cannulae 32, 34, 36 remain linked together with the flexible elements 38 and 40 (the distal end 36a of the cannula 36 is not seen in FIG. 13). The surgeon can freely manipulate the working cannulae 32, 34, and 36 for using them in association with various surgical tools (not shown). In other words, the flexible elements 38 and 40 which are passed through the working cannulae 32, always link the distal ends of the cannulae 32, 34, 36, while leaving for the cannulae a freedom of movement along the flexible elements 38 and 40.

In some situations the symptomatic site may be located relatively deep inside the patient's body. In order to avoid making a long incision that may be required for freedom of cannulae manipulation, the following procedure may be performed with the use of the device of the invention.

Figure 14:
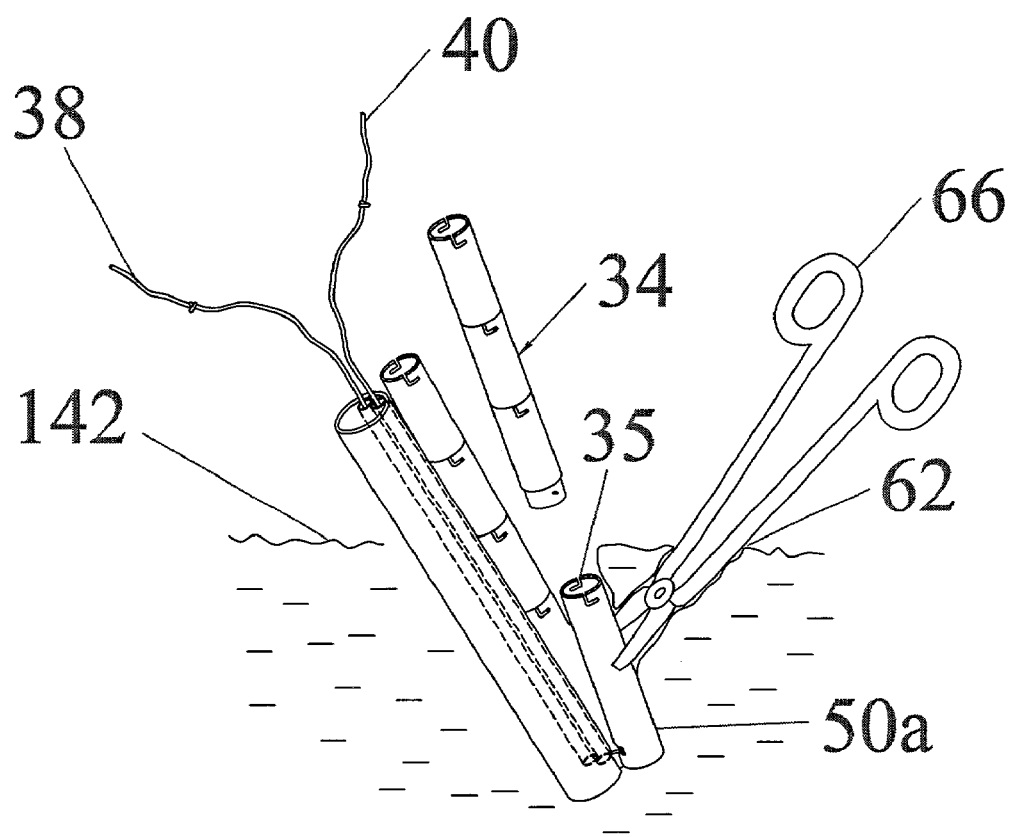
FIG. 14 is a three-dimensional view of the working cannulae after disconnecting several segments from one of the cannula and grasping the remaining part of the cannula with a forceps.
Figure 15:
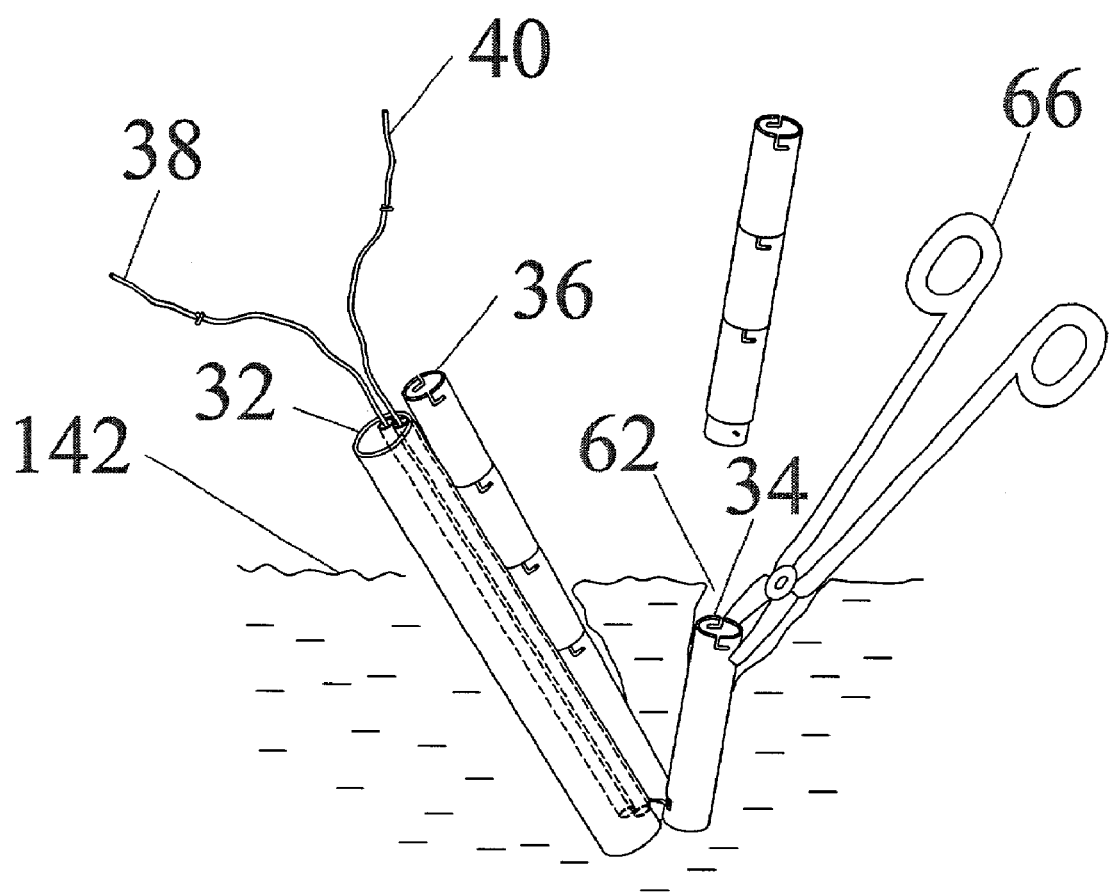
FIG. 15 is a view similar to FIG. 14 with the working cannula exposed through the second incision.

First, the surgeon pre-determines the most convenient places on the patient's body 142 for insertion of cannulae 34 and 36. With the cannula pack 154 in place, and the rubber band 152 removed, the surgeon makes a second incision 62, as it is shown in FIG. 13. As shown in FIG. 14, after the second incision 62 is made, the surgeon disconnects as many segments from cannula 34, as necessary to have the upper edge (35 in FIG. 14) of the remaining part of the cannula 34 (which in FIG. 14 is represented by a single lowermost segment 50a) as close to the patients skin as possible. Using an appropriate surgical instrument 66, the surgeon inserts it into the patient's body 142 through the aforementioned second incision 62, grabs the cannula 34, and using the elasticity of a human's skin, pulls the cannula 34 with a tool 66 under the skin until the cannula exposes through the incision 62, which is shown in FIG. 15.

Figure 16:
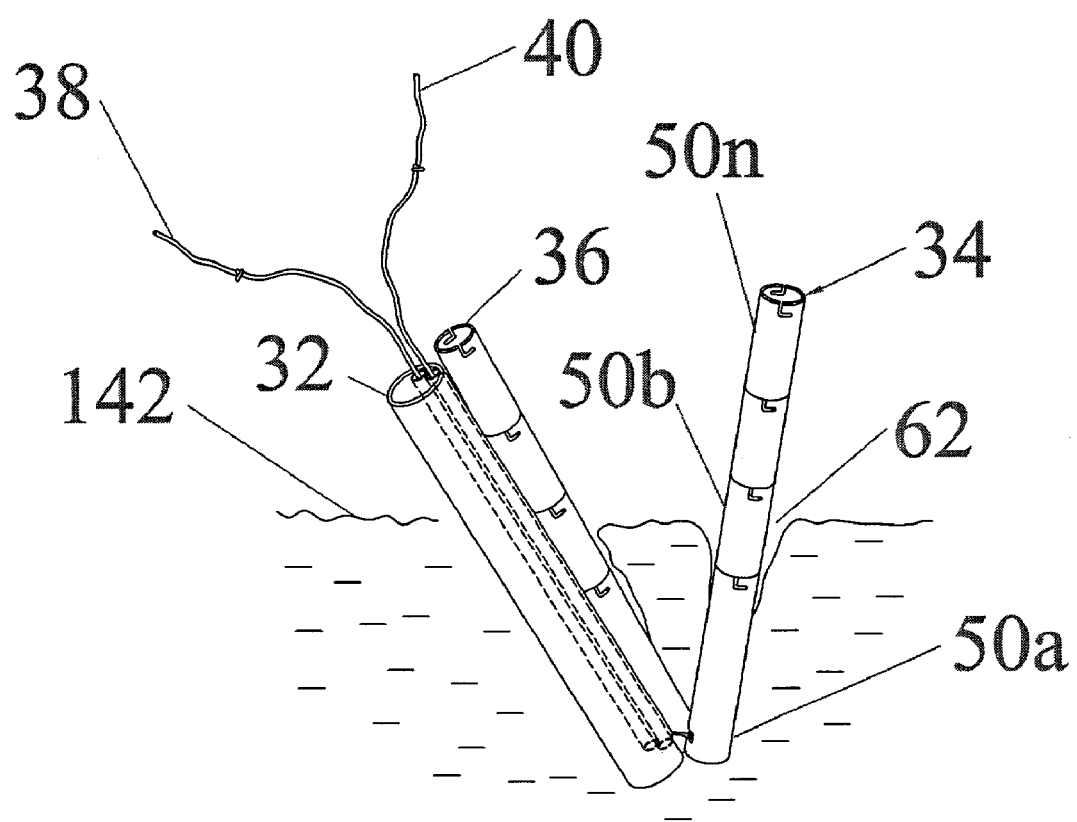
FIG. 16 is a view similar to FIG. 15 with the segments reconnected to the cannula exposed through the second incision.

Now the needed number of segments 50b, 50c ... can be reconnected to the cannula 34, as it shown in FIG. 16. Thus, the cannula 34 being still linked to the cannulae 32 and 36, is now can be used as a separate portal under the preferable angle to the cannula 32, keeping the incisions as short as possible.

Figure 17:
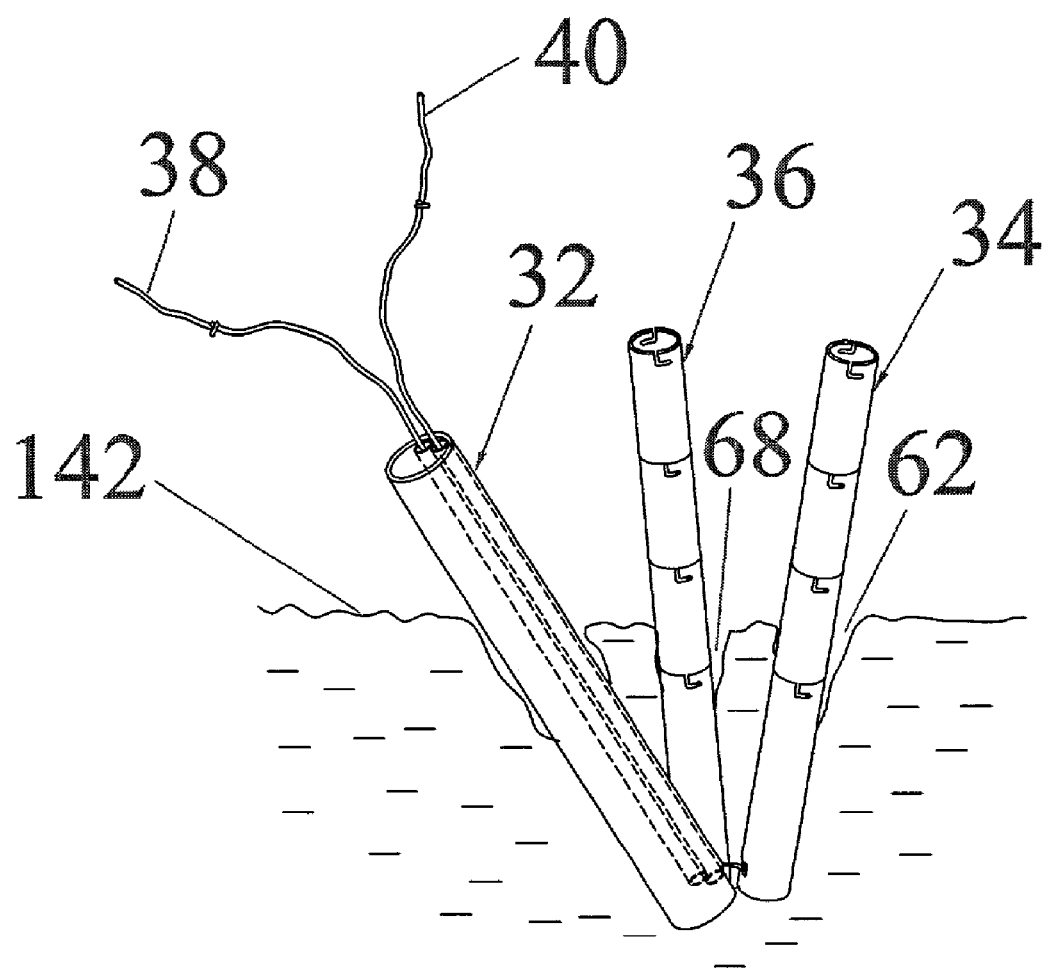
FIG. 17 is a view similar to FIG. 16 with all working cannulae exposed through individual incisions.

To perform the same procedure with cannula 36, the surgeon makes another incision 68, and repeats the steps described above, so that finally all cannulae are accessible through short individual incisions, while remain to be linked at their distal ends. This condition is shown in FIG. 17.

When it is necessary to reorient the cannulae and rejoin their distal ends, it is sufficient to pull up the proximal ends of the flexible elements 38 and 40. This operation can be done without any X-ray monitoring.

To remove cannulae from the patient's body 142 after completion of the surgery, it is enough to remove stoppers 46 and 48, e.g., by cutting them off, and to pull and remove side cannulae 34 and 36 together with their respective flexible elements 38 and 40 from the patient's body. The central cannula 32 can then be removed as well.

Figure 18:
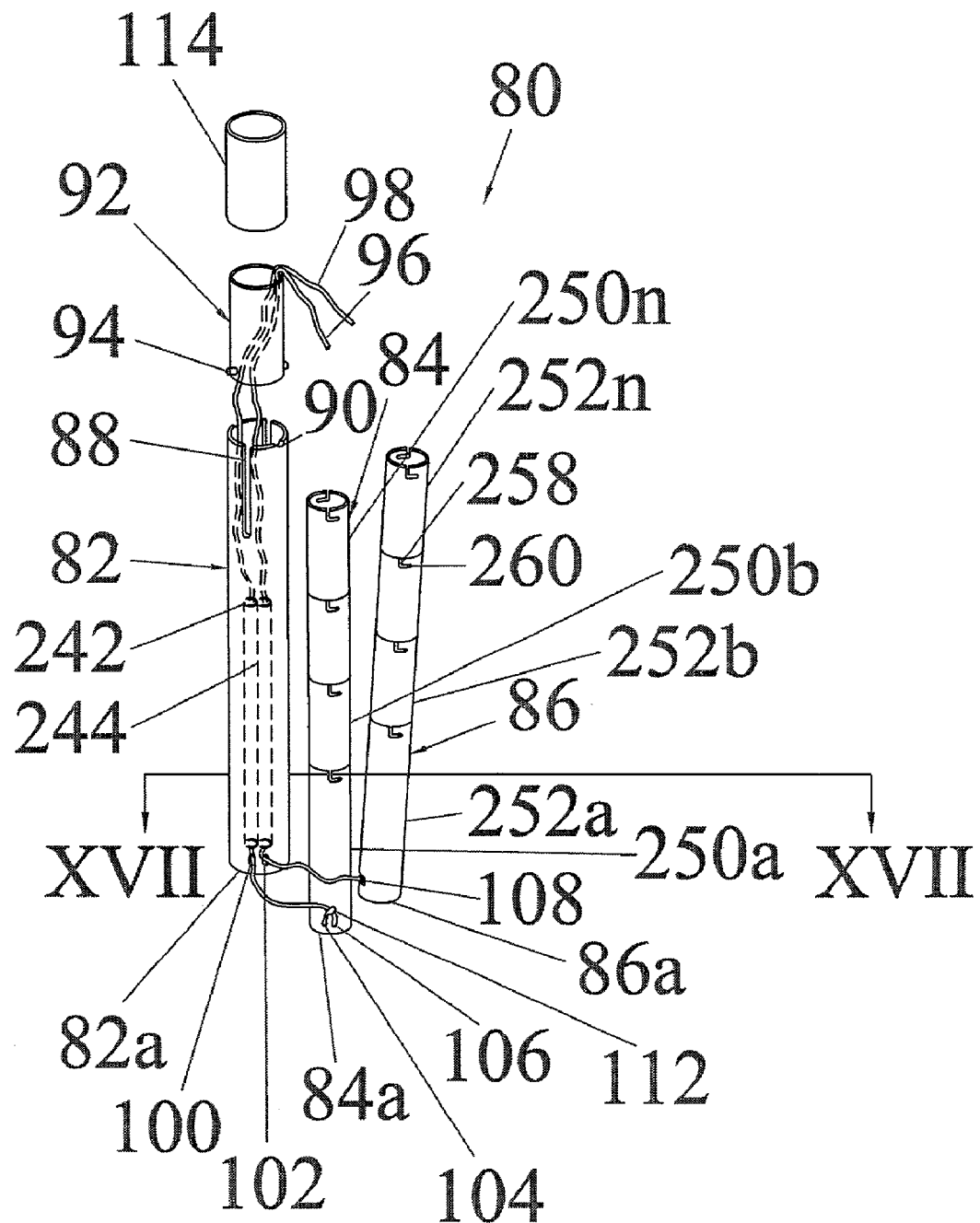
FIG. 18 is a three-dimensional exploded view of the device of the invention made in accordance with another embodiment.
Figure 19:
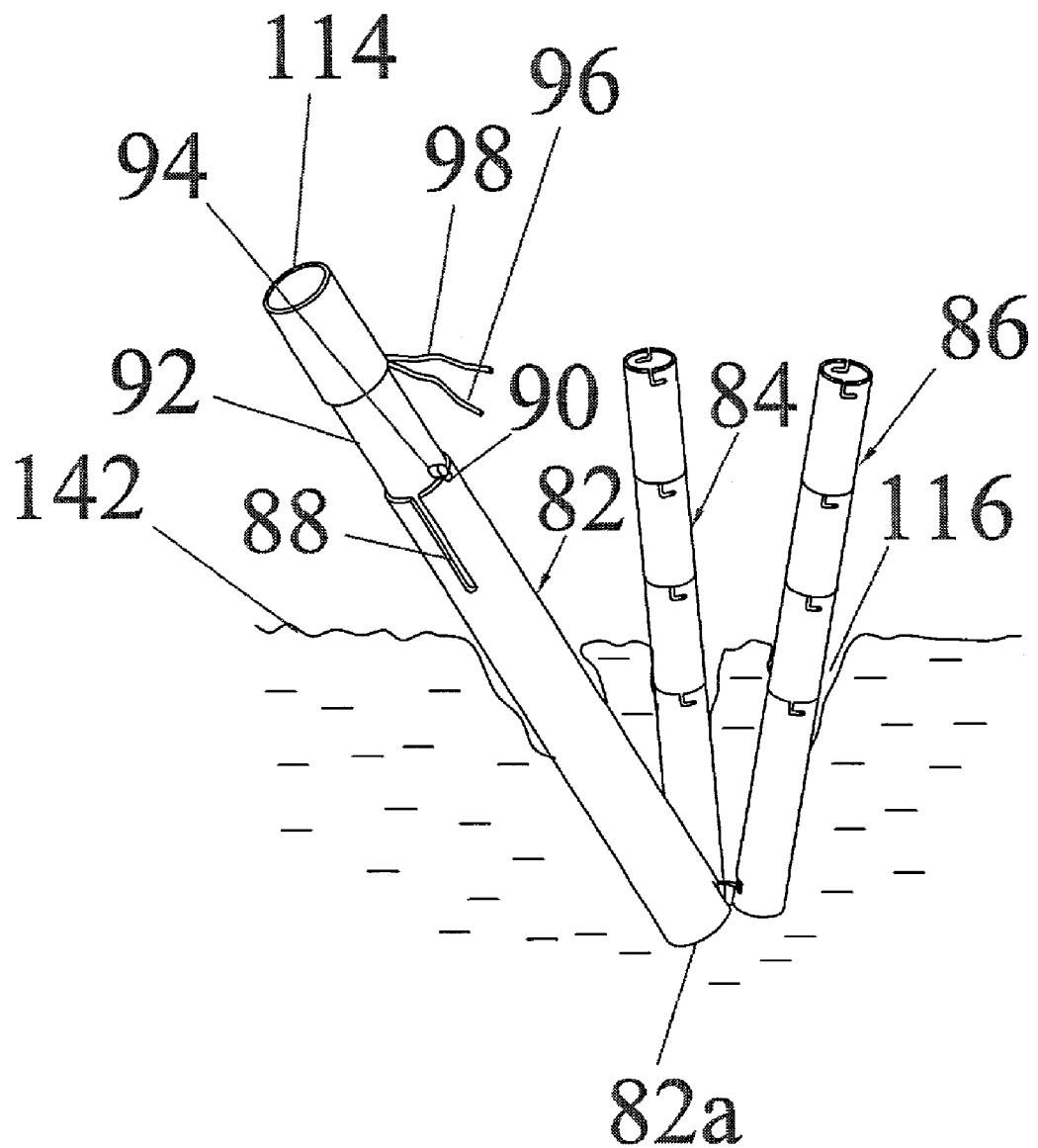
FIG. 19 is a three-dimensional view illustrating the device of FIG. 18 in a working position with distal ends of the cannulae being locked together
Figure 20:
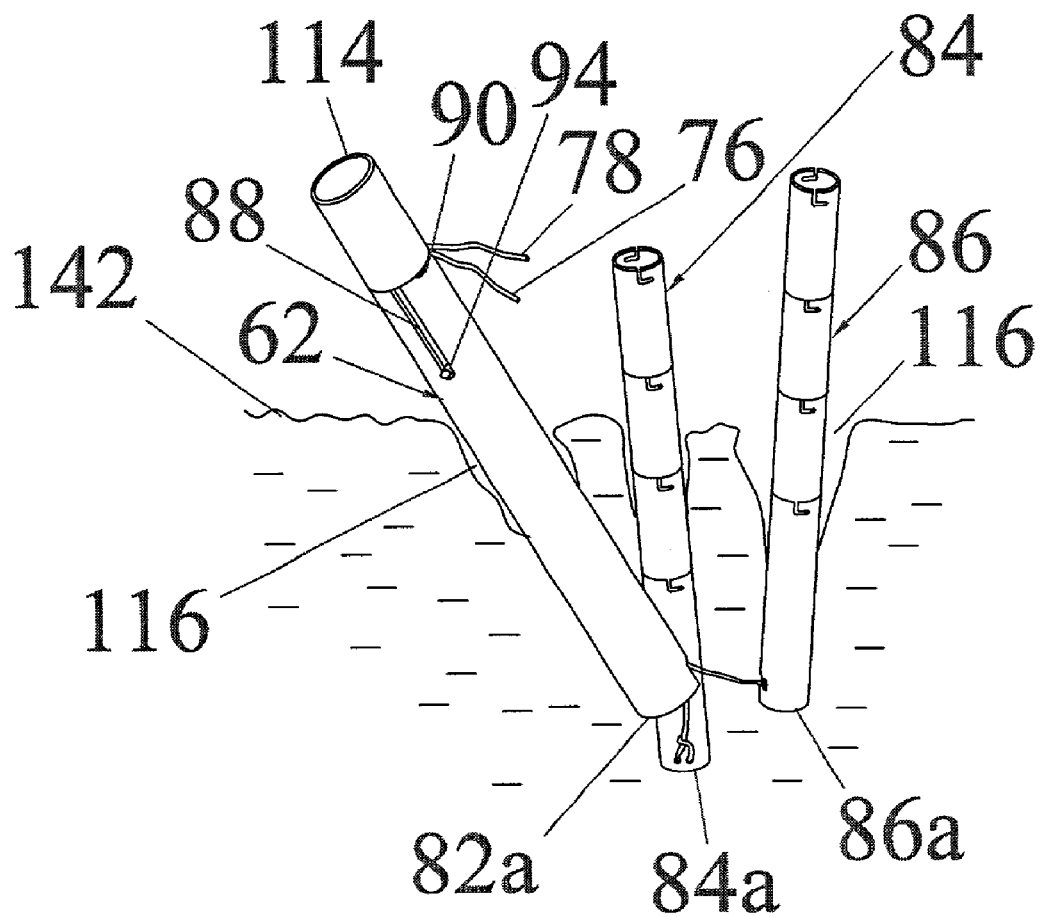
FIG. 20 is the same view as FIG. 19 with the distal ends of the cannulae being unlocked for manipulation.
Figure 21:
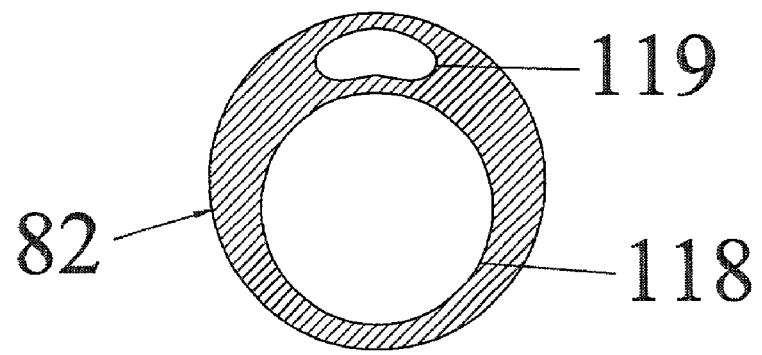
FIG. 21 is a sectional view along the line XVII—XVII of FIG. 18 illustrating a possible version of the guide channel for threads formed in the cannula sidewall.

Another embodiment of the multiportal device with linked segmented cannulae is shown in FIGS. 18 to 21, where FIG. 18 is a three-dimensional exploded view of the device consisting of three cannulae linked at their distal ends by flexible elements such as wires or threads, FIG. 19 is a three-dimensional view illustrating the device of FIG. 18 in a working position with distal ends of the cannulae being locked together, FIG. 20 is the same as FIG. 19 with the distal ends of the cannulae being unlocked for manipulation, and FIG. 21 is a sectional view along the line XVII—XVII of FIG. 18 illustrating a possible version of the guide channel for threads formed in the cannula wall.

In general, the device of this embodiment is similar to the one described above. Therefore those parts and units of the device of this embodiment, which are similar to analogous parts of the previous embodiment, will be designated with the same reference numerals with an addition of 200 and their description is omitted.

More specifically, as shown in FIG. 18, a multiportal device of the invention, which in general is designated by reference numeral 80, consists of three cannulae 82, 84, and 86. One of these cannulae, e.g., the cannula 82 has at least one long longitudinal groove 88 and at least one short longitudinal groove 90, both grooves being started from the upper edge of the cannula 82. The cannula 82 is also provided with a tubular latch 92 telescopically insertable with a sliding fit into the proximal end of the cannula 82. The latch 92 is provided with at least one short pin 94 extending outward radially from the outer wall of the tubular latch 92 and selectively insertable into the aforementioned grooves 88 and 90.

As in the previous embodiment shown in FIGS. 5, 11, and 13 to 17, the respective distal ends 82a, 84a, and 86a of the cannulae 82, 84, and 86 are linked together with the use of flexible elements such as wires or threads 96 and 98. The threads 96 and 98 are guided through the cannula 82 and their distal ends are passed through openings 100 and 102 formed in the sidewall of the cannula 82 close to the distal end thereof. The threads are then guided through the corresponding openings 104, 106 in the cannula 84 and openings 108, 110 in the cannula 86 (the opening 110 is not seen in FIG. 18). The distal free ends of the threads 96 and 98 associated with the cannulae 84 and 86, respectively, can be either fixed inside these cannulae or tied around the adjacent openings. This is shown in FIG. 18 by knot 112 on the cannula 84. The free proximal ends of the threads 96 and 98 protrude through both the cannula 82 and the tubular latch 92.

It is also possible to have the distal free ends of the threads guided along the cannula 82 back towards the proximal end of this cannula after passing them through both openings in the sidewalls of the respective cannulae 84 and 86 to form loops. In this case, both distal free ends of the threads 96 and 98 will protrude outward through cannula 82 and through the tubular latch 92 together with the proximal free ends of these threads.

Reference numeral 114 shown in FIG. 18 designates a tubular stopper that can be telescopically fitted with a tight fit onto the proximal end of the tubular latch 92 clutching the threads 96 and 98 between the walls of the tubular latch and 92 and the tubular stopper 114.

The multiportal device with linked cannulae made in accordance with the embodiment of FIG. 18 operates in the same manner as the device of the previous embodiment except for the steps of cannulae reorientation, fixation of the threads, and removing the stopper means.

The device is inserted into the incision 116 in the position shown in FIG. 19 with the pin 94 being located in the short longitudinal groove 90. In this state, the tubular latch 92 is in its uppermost position, and the threads 96 and 98 are tightened so that the cannula distal ends 82a, 84a, and 86a are hold together and cannot be moved apart, but still can be tilted with respect to each other. Location of the pin 94 in the short groove 90 prevents the tubular latch 92 from accidental angular displacement from the selected position.

For loosening the threads 96 and 98 in order to provide freedom of manipulation with the cannulae 82, 84, and 86, the pin 94 of the tubular latch 92 is removed from the short groove 90 and is inserted into the long groove 88, so that the tubular latch 92 assumes the lowermost position shown in FIG. 20. It is understood that in this position the loosened threads allow the surgeon to freely manipulate with the cannulae.

To remove the stopper means and let the threads to be able to freely pass through the cannula 82, it is enough to remove a tubular stopper 114 from the proximal end of the tubular latch 92.

FIG. 21 is a cross-sectional view along the line XVII—XVII of FIG. 18, which illustrates possible design of the cannula 82. It can be seen that in addition to the main central opening 118 for guiding surgical instrument, the wall of the cannula may have a thickened portion for forming a smaller through opening 119 for guiding the threads 96 and 98. In this case, the cross-section of the cannula 82 is not necessarily circular.

Thus it has been shown that the present invention provides a multiportal device with linked segmented cannulae for percutaneous surgery, which is simple in construction, reliable and simple in use, allows insertion of several cannulae and permanently maintaining them in controlled positions without resorting to additional X-ray. The device of the invention does not need the use of a separate guiding unit, does not cause excessive damage the tissue, allows the use of plastic materials, makes it possible to be used disposably and to increase the number of cannulae used simultaneously.

Although the invention has been shown and described with reference to specific embodiments, it is understood that these embodiments should not be construed as limiting the areas of application of the invention and that any changes and modifications are possible, provided these changes and modifications do not depart from the scope of the attached patent claims. For example, the cannula pack 154 can be inserted either without being bound or bound with another binding element. The flexible elements 38, 40, 96, 98 can be represented with a single flexible element, extended through all used cannulae 32, 34, 36, 82, 84, 86, and having its both ends protruding from the proximal end of the central cannula 32, 82. Two, or more than three, working cannulae can be used. The number of stackable segments that form the cannulae 34, 36, 84, 86 may vary. The segments can be connected by methods different from those described in the specification. The flexible elements 38, 40, 96, 98 can be made of a thread, wire, string, etc. They can be connected to the cannulae 34, 36, 84, 86 by welding, gluing, etc., or can be guided through a small-diameter tube attached to the inner wall of respective cannulae 34 and 36, as it is done for the central cannula 32. The central cannula 32, 82 may have flexible elements 38, 40, 96, 98 guided through the individual small-diameter tubes 42 and 44, or through a common small-diameter tube. The cross-sectional shape of the cannula shown in FIG. 21 with reference to the cannula 82 is also applicable to cannula 32. The tubular stopper 114 can be used instead of those designated by numbers 46 and 48. The tubular stopper 114 may be designed in a way that would not require its removal from the tubular latch 92 in order to let the flexible elements 38, 40, 96, 98 free. The short groove 90 may not be present in the cannula 32, or several short grooves can be made on the side of the long groove 88, allowing different degrees of flexibility of cannulae manipulation. The stopper means 46, 48, 114 can have different positions ensuring that distal ends of cannulae 32, 34, 36, 82, 84, 86 cannot be moved apart further than by predefined distance.

What we claim is:

1. A multiportal device with linked segmented cannulae for percutaneous surgery comprising:
    cannulae having sidewalls, distal ends, proximal ends, and central through openings, at least one segmented cannula of said cannulae comprising at least two tubular segments having means for connection to and disconnection from each other in said axial directions;
    flexible elongated members, having ends, said flexible elongated members are passed through at least one cannula of said cannulae and link said cannulae together, allowing each cannula to move along said flexible elongated members and tilt relative to each other, wherein said ends of said flexible elongated members protrude from a proximal end of at least one cannula, said ends of said flexible elongated members being provided with stopper means for preventing full passage of said flexible elongated members through said at least one cannula.

2. The multiportal device of claim 1, wherein said cannulae have side through openings in said sidewalls close to said distal ends, said flexible elongated members being guided through said side through openings for linking said cannulae together.

3. The multiportal device of claim 2, wherein said ends of said flexible elongated members that are guided through said side through openings are attached to said sidewalls of said cannulae except said at least one cannula.

4. The multiportal device of claim 3, wherein said at least one cannula has at least one guide tube, attached to a sidewall thereof for guiding said flexible elongated members.

5. The multiportal device of claim 4, further comprising a binding member for binding said cannulae into a single pack.

6. The multiportal device of claim 4, wherein said at least one cannula is provided with a tubular latch telescopically insertable with a sliding fit into a proximal end of said at least one cannula and with means for securing said tubular latch in said at least one cannula in a first position, in which said flexible elongated members are tightened preventing said distal ends from moving apart from each other and in at least a second position, in which said flexible elongated members are loosened allowing said distal ends to be moved apart from each other.

7. The multiportal device of claim 6, further comprising a binding member for binding said cannulae into a single pack.

8. The multiportal device of claim 3, wherein said at least one cannula has a through longitudinal passage formed in a sidewall of said at least one cannula for guiding said flexible elongated members.

9. The multiportal device of claim 8, further comprising a binding member for binding said cannulae into a single pack.

10. The multiportal device of claim 8, wherein said at least one cannula is provided with a tubular latch telescopically insertable with a sliding fit into a proximal end of said at least one cannula and with means for securing said tubular latch in said at least one cannula in a first position, in which said flexible elongated members are tightened preventing said distal ends from moving apart from each other and in at least a second position, in which said flexible elongated members are loosened allowing said distal ends to be moved apart from each other.

11. The multiportal device of claim 10, further comprising a binding member for binding said cannulae into a single pack.

12. The multiportal device of claim 2, wherein said ends of said flexible elongated members that are guided through said side through openings are guided back to a proximal end of said at least one cannula and protrude through said proximal end of said at least one cannula.

13. The multiportal device of claim 12, wherein said at least one cannula has at least one guide tube attached to a sidewall thereof for guiding said flexible elongated members.

14. The multiportal device of claim 13, further comprising a binding member for binding said cannulae into a single pack.

15. The multiportal device of claim 13, wherein said at least one cannula is provided with a tubular latch telescopically insertable with a sliding fit into a proximal end of said at least one cannula and with means for securing said tubular latch in said at least one cannula in a first position, in which said flexible elongated members are tightened preventing said distal ends from moving apart from each other and in at least a second position, in which said flexible elongated members are loosened allowing said distal ends to be moved apart from each other.

16. The multiportal device of claim 15, further comprising a binding member for binding said cannulae into a single pack.

17. The multiportal device of claim 12, wherein said at least one cannula has a through longitudinal passage formed in a sidewall of said at least one cannula for guiding said flexible elongated members.

18. The multiportal device of claim 17, further comprising a binding member for binding said cannulae into a single pack.

19. The multiportal device of claim 17, wherein said at least one cannula is provided with a tubular latch telescopically insertable with a sliding fit into a proximal end of said at least one cannula and with means for securing said tubular latch in said at least one cannula in a first position, in which said flexible elongated members are tightened preventing said distal ends from moving apart from each other and in at least a second position, in which said flexible elongated members are loosened allowing said distal ends to be moved apart from each other.

20. The multiportal device of claim 19, further comprising a binding member for binding said cannulae into a single pack.

21. A multiportal device with linked segmented cannulae for percutaneous surgery comprising:
a central cannula having a sidewall, a distal end, a proximal end, and a central through opening;
two side cannulae, each having a sidewall, a distal end, a proximal end, and a central through opening, at least one of said two side cannula comprising at least two tubular segments having means for connection to and disconnection from each other in said axial direction of each of said two side cannulae; and
two flexible elongated members, having ends, said flexible elongated members are passed through said central through opening of said central cannula and link said central cannula with said two side cannulae together, allowing said central cannula and said two side cannulae to both move along said two flexible elongated members and tilt relative to each other.

22. The multiportal device of claim 21, wherein said ends of said flexible elongated members protrude from said proximal end of said central cannula, said ends of said two flexible elongated members being provided with stopper means for preventing full passage of said two flexible elongated members through said central cannula.

23. The multiportal device of claim 22, wherein said central cannula and said two side cannulae have side through openings in said sidewalls thereof close to said distal ends thereof, said two flexible elongated members being guided through said side through openings for linking said central cannula and said two side cannulae together.

24. The multiportal device of claim 23, wherein said ends of said two flexible elongated members that are guided through said side through openings are attached to said sidewalls of said two side cannulae.

25. The multiportal device of claim 24, wherein said central cannula has at least one guide tube attached to said sidewall of said central cannula for guiding said two flexible elongated members.

26. The multiportal device of claim 25, further comprising a binding member for binding said central cannula and said two side cannulae into a single pack.

27. The multiportal device of claim 25, wherein said central cannula is provided with a tubular latch telescopically insertable with a sliding fit into said proximal end of said central cannula and with means for securing said tubular latch in said central cannula in a first position, in which said two flexible elongated members are tightened preventing said distal ends of said central cannula and said two side cannulae from moving apart from each other and in at least a second position, in which said two flexible elongated members are loosened allowing said distal ends of said central cannula and said two side cannulae to be moved apart from each other.

28. The multiportal device of claim 27, further comprising a binding member for binding said cannulae into a single pack.

29. The multiportal device of claim 24, wherein said central cannula has a through longitudinal passage formed in a sidewall of said central cannula for guiding said two flexible elongated members.

30. The multiportal device of claim 29, further comprising a binding member for binding said central cannula and said two side cannulae into a single pack.

31. The multiportal device of claim 29, wherein said central cannula is provided with a tubular latch telescopically insertable with a sliding fit into said proximal end of said central cannula and with means for securing said tubular latch in said central cannula in a first position, in which said two flexible elongated members are tightened preventing said distal ends of said central cannula and said two side cannulae from moving apart from each other and in at least a second position, in which said two flexible elongated members are loosened allowing said distal ends of said central cannula and said two side cannulae to be moved apart from each other.

32. The multiportal device of claim 31, further comprising a binding member for binding said central cannula and said two side cannulae into a single pack.

33. The multiportal device of claim 23, wherein said ends of said two flexible elongated members that are guided through said side through openings are guided back to said proximal end of said central cannula and protrude through said proximal end of said central cannula.

34. The multiportal device of claim 33, wherein said central cannula has at least one guide tube attached to said sidewall of said central cannula for guiding said two flexible elongated members.

35. The multiportal device of claim 34, further comprising a binding member for binding said central cannula and said two side cannulae into a single pack.

36. The multiportal device of claim 34, wherein said central cannula is provided with a tubular latch telescopically insertable with a sliding fit into said proximal end of said central cannula and with means for securing said tubular latch in said central cannula in a first position, in which said two flexible elongated members are tightened preventing said distal ends of said central cannula and said two side cannulae from moving apart from each other and in at least a second position, in which said two flexible elongated members are loosened allowing said distal ends of said central cannula and said two side cannulae to be moved apart from each other.

37. The multiportal device of claim 36, further comprising a binding member for binding said central cannula and said two side cannulae into a single pack.

38. The multiportal device of claim 33, wherein said central cannula has a through longitudinal passage formed in said sidewall of said central cannula for guiding said two flexible elongated members.

39. The multiportal device of claim 38, further comprising a binding member for binding said central cannula and said two side cannulae into a single pack.

40. The multiportal device of claim 38, wherein said central cannula is provided with a tubular latch telescopically insertable with a sliding fit into said proximal end of said central cannula and with means for securing said tubular latch in said central cannula in a first position, in which said two flexible elongated members are tightened preventing said distal ends of said central cannula and said two side cannulae from moving apart from each other and in at least a second position, in which said two flexible elongated members are loosened allowing said distal ends of said central cannula and said two side cannulae to be moved apart from each other.

41. The multiportal device of claim 40, further comprising a binding member for binding said central cannula and said two side cannulae into a single pack.

42. The multiportal device of claim 21, further comprising a binding member for binding said cannulae into a single pack.

* * * * *